United States Patent [19]
Castel et al.

[11] Patent Number: 4,690,141
[45] Date of Patent: Sep. 1, 1987

[54] FRESNEL LENS LIGHT APPLICATOR

[76] Inventors: John C. Castel, c/o Physio Technology, Inc., 1925 W. 6th St., Topeka, Kans. 66606; Richard G. Kerwin, 1004 Elmhurst Rd., Prospect Hts., Ill. 60070

[21] Appl. No.: 776,354

[22] Filed: Sep. 16, 1985

[51] Int. Cl.[4] .......................... A61N 5/00; F21V 5/04; G02B 3/08

[52] U.S. Cl. .................................. 128/396; 128/397; 350/452; 362/259; 362/268

[58] Field of Search ................... 128/395–398, 128/24.1; 350/452; 362/259, 268, 278, 326, 330, 331, 333

[56] References Cited

U.S. PATENT DOCUMENTS

| | | | |
|---|---|---|---|
| 2,183,726 | 12/1939 | Sommer et al. | 128/24.1 |
| 3,234,376 | 2/1966 | Ceglia | 362/330 |
| 3,334,958 | 8/1967 | Appeldorn | 362/331 X |
| 3,670,260 | 6/1972 | Koester et al. | 128/395 X |
| 3,900,034 | 8/1975 | Katz et al. | 128/395 |
| 4,232,678 | 11/1980 | Skovajsa | 128/395 |
| 4,321,930 | 3/1982 | Jobsis et al. | 128/633 |
| 4,574,338 | 3/1986 | Takasaki et al. | 326/278 |

FOREIGN PATENT DOCUMENTS 2740969 3/1979 Fed. Rep. of Germany.

OTHER PUBLICATIONS

"Nogi", (Magnetic Flux Sources for Medical and Biological Use), publd. Aug. 1980, copy 128/1.3.

*Primary Examiner*—Anton O. Oechsle

[57] ABSTRACT

A therapeutic laser radiation applicator including a laser energy radiator, a fresnel lens, and structure for mounting the fresnel lens in preselected association with the laser radiator for refracting a portion of the laser radiation to a preselected beam configuration adapted to provide a therapeutic tissue irradiation pattern. The support is preferably flexible to accommodate the applicator to the surface configuration of the tissue to be treated. The fresnel lens elements are preferably formed of a flexible material and, in the illustrated embodiment are formed integrally in a sheet of light-transmissive synthetic resin. The fresnel lens structure may comprise one or more fresnel lens elements in series light-diffracting relationship.

19 Claims, 4 Drawing Figures

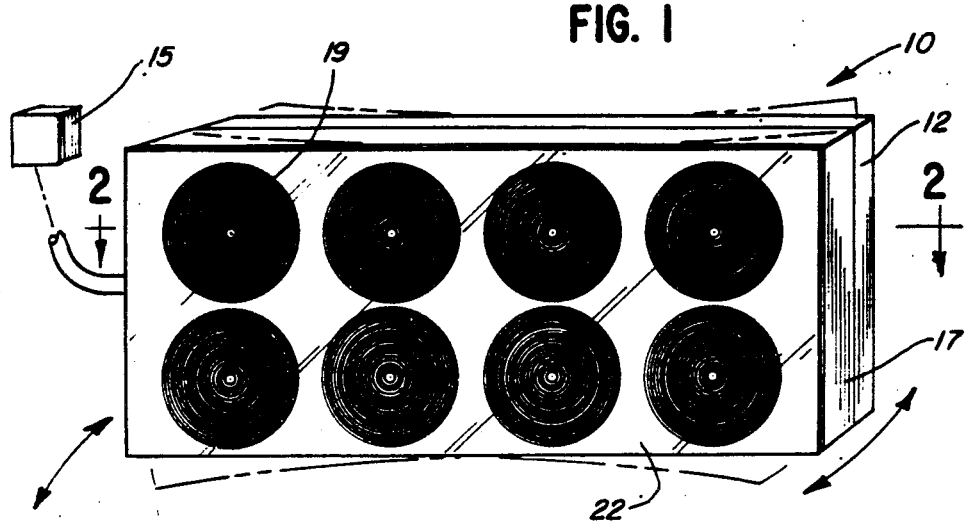
FIG. 1
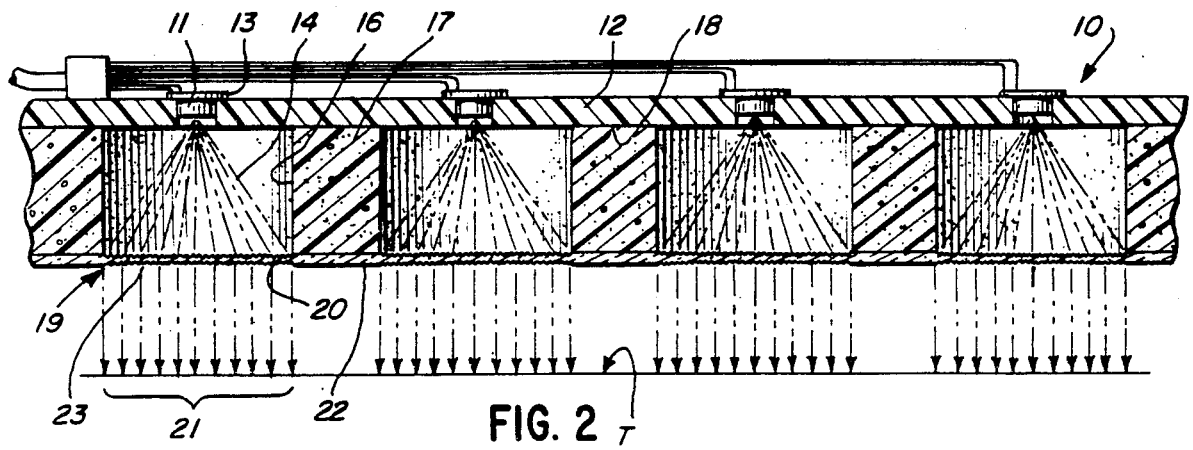
FIG. 2
FIG. 3 FIG. 4
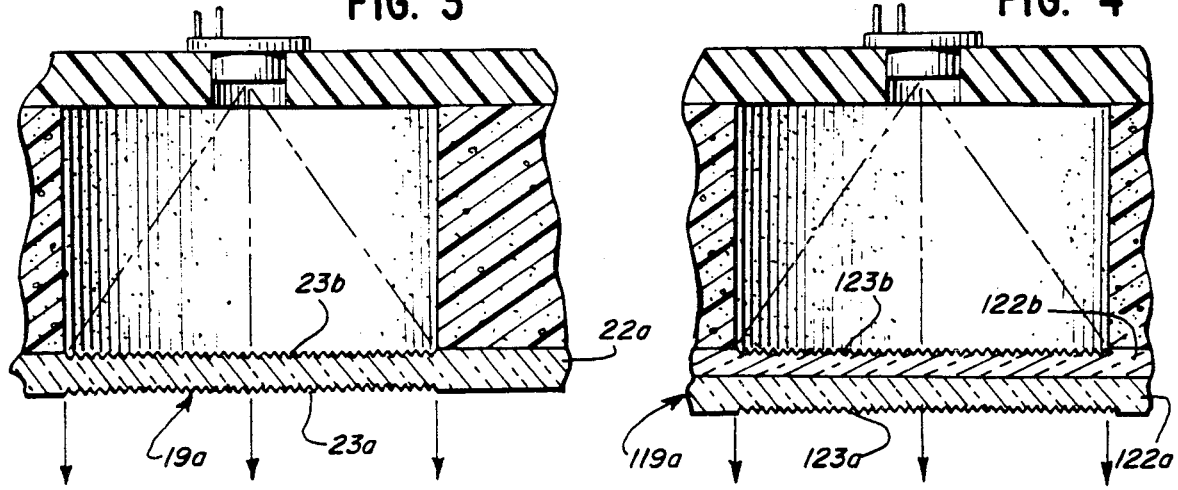

ical field

FRESNEL LENS LIGHT APPLICATOR

TECHNICAL FIELD

This invention relates to laser light applicators and in particular to means for controlling the characteristics of the applied laser light.

BACKGROUND ART

The use of laser light radiation in the treatment of tissue and nerve stimulation is well known. Such treatment of tissue may be effected by use of a single laser light source, or by means of devices employing a plurality of such sources in distributed side-by-side arrangement. Further, such multiple laser devices may be flexible so as to accommodate themselves to the surface of the tissue being stimulated.

The radiation pattern of laser light delivered from a laser source, such as a diode, spreads therefrom in a generally conical manner. It has been found, however, that the light divergent angles along perpendicular axes, e.g. x and y axes, differs so that the transverse cross section thereof is elliptical.

DISCLOSURE OF INVENTION

The present invention comprehends the provision in such a laser light generating means of means for controlling the laser light emanation so as to provide a desired treatment pattern.

More specifically, the invention comprehends the provision of fresnel lens means interposed between the laser light source and the surface to be treated for defining a preselected desired treatment pattern.

More specifically, the invention comprehends the provision of a therapeutic laser radiation applicator including means for producing laser radiation, a fresnel lens, and means for mounting the fresnel lens in preselected association with the laser radiation means for refracting a pattern of the laser radiation to a preselected beam configuration adapted to provide a desired therapeutic tissue irradiation pattern.

In the illustrated embodiment, a plurality of such fresnel lens means may be mounted in series for augmented control of the laser beam.

In one illustrated embodiment, a pair of fresnel lenses are mounted in back-to-back relationship.

The fresnel lens means may be arranged to collimate the laser radiation in the application pattern.

The fresnel lens means may be flexible, and in the illustrated embodiment, the fresnel lens means is formed as an embossed body of flexible synthetic resin.

The support for the fresnel lens means may be flexible and, in the illustrated embodiment, the flexible fresnel lens means is adhesively secured to one surface of the flexible support so as to provide a flexible applicator structure.

The applicator structure may include a plurality of laser light sources and corresponding fresnel lens means in side-by-side distributed relationship so as to provide concurrent laser light radiation in treating an extended area of tissue.

The therapeutic laser radiation applicator of the present invention is extremely simple and economical of construction while yet providing the highly desirable features discussed above.

BRIEF DESCRIPTION OF THE DRAWING

Other features and advantages of the invention will be apparent from the following description taken in connection with the accompanying drawing wherein:

FIG. 1 is a perspective view of a therapeutic laser radiation applicator embodying the invention;

FIG. 2 is a longitudinal section thereof taken substantially along the line 2—2 of FIG. 1;

FIG 3. is a fragmentary section illustrating a modified form of the laser radiation applicator utilizing a modified form of fresnel lens means; and FIG. 4 is a fragmentary section similar to that of FIG. 3, but illustrating a further modified form of laser radiation applicator utilizing still another form of fresnel lens means.

BEST MODE FOR CARRYING OUT THE INVENTION

In the illustrative embodiment of the invention as disclosed in the drawing, a therapeutic laser radiation applicator generally designated 10 is provided for directing laser light energy against a surface T of tissue to be stimulated by the laser light radiation.

The applicator is adapted to be placed in facial contact with the tissue surface, or spaced therefrom where such contact would be inimical as neither aggravating nor infecting the tissue.

Applicator 10 is provided with at least one laser light source 11, such as a conventional laser light diode, and in the illustrated embodiment, eight such laser diode light sources are provided mounted in spaced, side-by-side distribution in a carrier 12. The carrier is provided with a corresponding plurality of openings 13 through which the diode partially extends and from which laser light radiation 14 emanates in the conventional diverging manner, as illustrated in FIG. 2. The diodes are energized from a suitable electrical energization control 15. Alternatively, the laser illumination may be delivered to the openings 13 by means of light pipes, with the laser radiation being generated at the control 15 and distributed to the openings for radiation therefrom by means of conventional light pipes (not shown). In either case, the laser light radiates from the source at openings 13 in the indicated diverging pattern. As will be obvious to those skilled in the art, the laser source at opening 13 may include both the diode radiation means and the light pipe means, if desired.

Radiation 14 is directed through an opening 16 in a foam spacer 17 secured to the bottom surface 18 of carrier 12. In the illustrated embodiment, carrier 12 is formed of a flexible sheet material, such as Mylar, synthetic resin, nylon, etc.

A fresnel lens means generally designated 19 is provided across the lower end 20 of each opening 16 for redirecting the laser radiation to a preselected desired pattern 21 on the tissue surface T.

In the illustrated embodiment, the fresnel lens means 19 is embossed in a light-transmissive, synthetic resin sheet 22. As illustrated in FIG. 2, the lens means 19 may be defined by a single embossed lens pattern 23 on one face of the sheet 22.

Alternatively, as illustrated in FIG. 3, a modified form of fresnel lens means 19a may be defined by a sheet 22a having a first fresnel lens pattern 23a on its lower surface, and a second fresnel lens pattern 23b on its upper surface to provide further refraction of the laser radiation rays in controlling the emanation pattern 21.

Referring to FIG. 4, still another form of fresnel lens means generally designated 119a is shown to comprise a pair of sheets 122a and 122b. Sheet 122a has a single fresnel lens pattern 123a disposed on its lower surface and sheet 122b has a single fresnel lens pattern 123b disposed on its upper surface. The sheets may be juxtaposed in facial engagement, as shown in FIG. 4.

As will be obvious to those skilled in the art, any desired plurality of fresnel lens elements may be provided in combination. Illustratively, it has been found that the use of three such fresnel lenses in series provides for improved collimation of the laser light radiation and, thus, provides improved therapeutic effect where such collimation of the radiation is desired.

The diameter of the support opening 16 is determined by the height of the support 17 and the angle of divergence of the radiation from the laser light source 11 in the carrier opening 13. As indicated above, it is common that the divergence angles of the conventional laser diodes may differ along perpendicular axes as to provide an elliptical emanation pattern. The fresnel lens means 19 may be arranged to convert the elliptical pattern into a circular one.

As will be obvious to those skilled in the art, the parameters of the application may be utilized to determine the desired fresnel lens configuration in the conventional manner. Thus, determination of the divergence angle for the light source, the distance between the light source and the fresnel lens means, and the spacing of the fresnel lens means from the tissue surface T permit ready determination of the fresnel lens configuration in the normal manner.

Broadly, the use of the fresnel lens means 19 permits redirecting the diverging light from the laser light source to define the desired pattern on the tissue surface. Where the divergence angle is equal about the axis of the source, a single fresnel lens may be utilized as long as the focal length of the lens is longer than the distance between the lens and the surface T.

In the configuration of FIG. 4, the lens 123b may redirect the divergence along one axis and lens 123a may direct the divergence along an axis perpendicular thereto. As indicated above, a third fresnel lens may be utilized to collimate the diffracted radiation.

The invention comprehends the forming of the fresnel lens means in a flexible material so as to permit accommodation of the applicator to the surface of the tissue T to be treated. As will be obvious to those skilled in the art, where the applicator is intended to be used in treating flat surface areas, the individual fresnel lenses may be formed of a rigid material, such as glass, within the broad scope of the invention. Further, illustratively, where the fresnel lenses are formed of a rigid material, limited flexibility to the entire applicator may be provided by the use of the flexible support and carrier means of applicator 10.

As shown in FIG. 1, the fresnel lens and support openings may be closely juxtaposed so as to provide facilitated delivery of the laser radiation energy over the desired tissue surface.

The foregoing disclosure of specific embodiments is illustrative of the broad inventive concepts comprehended by the invention.

We claim:

1. A therapeutic laser radiation applicator comprising:
   means for providing laser radiation in an elliptical transverse distribution; and
   means for converting the elliptical transverse distribution of the laser radiation into a circular distribution thereof comprising at least two axially spaced fresnel lenses, and means for mounting the fresnel lenses in preselected association with said laser radiation means for refracting a portion of a laser radiation to said circular distribution adapted to provide a therapeutic tissue irradiation pattern.

2. The therapeutic laser radiation applicator of claim 1 wherein at least three axially spaced fresnel lenses are mounted in series for refracting the refracted laser radiation in forming the desired beam configuration.

3. The therapeutic laser radiation applicator of claim 1 wherein the fresnel lenses are disposed in back-to-back relationship.

4. The therapeutic laser radiation applicator of claim 1 wherein said fresnel lenses and said means for mounting the lens are flexible.

5. A therapeutic laser radiation applicator comprising:
   a support provided with a through opening;
   means for providing laser radiation;
   means for mounting said laser radiating means at one end of said through opening to direct laser radiation therethrough; and
   means for converting the elliptical transverse distribution of the laser radiation into a circular distribution thereof comprising at least two axially spaced fresnel lenses, and means for mounting the fresnel lenses in preselected association with said laser radiation means for refracting a portion of the laser radiation to said circular distribution adapted to provide a therapeutic tissue irradiation pattern.

6. The therapeutic radiation laser applicator of claim 5 wherein said support is flexible.

7. The therapeutic radiation laser applicator of claim 5 wherein said fresnel lens comprises an embossed body of synthetic resin.

8. The therapeutic radiation laser applicator of claim 5 wherein said fresnel lens comprise an embossed flexible sheet of synthetic resin.

9. The therapeutic radiation laser applicator of claim 5 wherein said means for mounting the laser radiation means comprises a body of synthetic resin.

10. The therapeutic radiation laser applicator of claim 5 wherein said means for mounting the laser radiation means comprises a flexible body of synthetic resin.

11. A therapeutic laser radiation applicator comprising:
    a support provided with a through opening;
    means for providing laser radiation;
    means for mounting said laser radiation means at one end of said through opening to direct laser radiation therethrough;
    a fresnel lens; and
    means for mounting the fresnel lens at the other end of said through opening for refracting a portion of the laser radiation to a modified preselected beam characteristic adapted to provide a therapeutic tissue irradiation pattern, said support being formed of foam material.

12. A therapeutic laser radiation applicator comprising:
    a support provided with a through opening;
    means for providing laser radiation;
    means for mounting said laser radiation means at one end of said through opening to direct laser radiation therethrough;

a fresnel lens; and means for mounting the fresnel lens at the other end of said through opening for refracting a portion of the laser radiation to a modified preselected beam characteristic adapted to provide a therapeutic tissue irradiation pattern, said fresnel lens comprising an embossed body of synthetic resin adhesively secured to said support.

13. A therapeutic laser radiation applicator comprising:

a support provided with a plurality of distributed through openings;

a corresponding plurality of means for producing laser radiation;

means for mounting said laser radiation means one each at one end of the respective through openings;

a corresponding plurality of fresnel lenses; and means for mounting the fresnel lenses one each at the other end of the respective through openings for refracting a portion of the laser radiation to a plurality of preselected beams adapted to provide concurrent therapeutic tissue irradiation.

14. The therapeutic laser radiation applicator of claim 13 wherein at least one additional fresnel lens is mounted in series with each of said first named fresnel lenses for further refracting the refracted laser radiation in forming the desired beams.

15. The therapeutic laser radiation applicator of claim 13 where said fresnel lenses are juxtaposed laterally.

16. The therapeutic laser radiation applicator of claim 13 wherein said fresnel lenses are generally flat and are arranged in flatwise juxtaposition.

17. The therapeutic laser radiation applicator of claim 13 wherein the axes of said lenses are generally parallel.

18. The therapeutic laser radiation applicator of claim 13 wherein said laser radiation means comprises diode means.

19. The therapeutic laser radiation applicator of claim 13 wherein said laser radiation means comprises radiation conducting means.

* * * * *